United States Patent
Conover

(10) Patent No.: US 10,582,705 B2
(45) Date of Patent: Mar. 10, 2020

(54) FOOTWEAR OUTER SOLE DISINFECTANT COMPRISING A QUATERNARY AMMONIUM BIOCIDE

(71) Applicant: Donald Conover, Buffalo Grove, IL (US)

(72) Inventor: Donald Conover, Buffalo Grove, IL (US)

( * ) Notice: Subject to any disclaimer, the term of this patent is extended or adjusted under 35 U.S.C. 154(b) by 80 days.

(21) Appl. No.: 16/006,267

(22) Filed: Jun. 12, 2018

(65) Prior Publication Data

US 2019/0373883 A1     Dec. 12, 2019

(51) Int. Cl.
  *C11D 1/62* (2006.01)
  *A01N 25/02* (2006.01)
  *A01N 33/12* (2006.01)

(52) U.S. Cl.
  CPC .......... *A01N 25/02* (2013.01); *A01N 33/12* (2013.01)

(58) Field of Classification Search
  CPC .... C11D 1/62; C11D 3/33; C11D 3/48; C11D 3/50; C11D 11/0023; C11D 17/08
  See application file for complete search history.

(56) References Cited

U.S. PATENT DOCUMENTS

| | | | |
|---|---|---|---|
| 2005/0065059 A1* | 3/2005 | Roselle | A47L 23/00 510/475 |
| 2005/0098759 A1* | 5/2005 | Frankenbach | D06M 7/00 252/8.91 |
| 2013/0052249 A1* | 2/2013 | Sipponen | A01N 37/08 424/405 |

FOREIGN PATENT DOCUMENTS

| | | |
|---|---|---|
| CA | 2315892 | 2/2001 |
| CA | 2397152 | 8/2001 |
| WO | 9856888 | 12/1998 |

OTHER PUBLICATIONS

Sigma-Aldrich "Ethylenediamine-N,W-disuccinic acid trisodium salt solution trisodium salt solution"; Nov. 6, 2017; entire document; downloaded Jul. 23, 2019: https://www.sigmaaldrich.com/eatalog/product/aldrich/92698lang=en®ion=US.
Lonza "Dantogard® Household and Industrial Preservative" Oct. 15, 2004.
Lonza "Proxel® GXL Preservative" Jun. 25, 2015.
The International Search Report and the Written Opinion of the International Searching Authority dated Aug. 21, 2019 for International Application No. PCT/US19/36690.

\* cited by examiner

*Primary Examiner* — Charles I Boyer
(74) *Attorney, Agent, or Firm* — Timothy M. McCarthy; Clark Hill PLC

(57) ABSTRACT

A solution for disinfecting the outer soles of footwear is described. The solution comprises a microbial inhibitor, a malodor counteractant, a fragrance, and a solvent. The solution can comprise an odor neutralizer, a chelating agent, a preservative, a surfactant, a fragrance, a tackifier, a biocide; and a solvent.

8 Claims, No Drawings

FOOTWEAR OUTER SOLE DISINFECTANT COMPRISING A QUATERNARY AMMONIUM BIOCIDE

FIELD OF THE INVENTION

This invention is directed to the field of disinfecting footwear and protecting homes from tracked-in bacteria.

BACKGROUND OF THE INVENTION

The outer sole of a person's footwear can hold numerous bacteria. These bacteria are picked up by, for examples, contact with animal waste while walking outdoors, contact with bacteria on the floor of a public restroom, and contact with bacteria on the floor of public places such as grocery stores and doctor's offices. Bacteria picked up on one's shoes can be tracked into a residence and transferred to that residence, which can lead to infections. The problem is especially acute for residences where small children live, who spend time crawling on the floor after visitors have tracked in bacteria from outside the home.

Accordingly, there is a need for a disinfectant for the outer soles of people's footwear. For purposes of the following description, "footwear" includes any outer covering for feet, such as shoes, boots, and sandals, whether used by a human or by an animal such as a household pet.

SUMMARY OF THE INVENTION

The preferred embodiment of the method of the present invention comprises a spray or solution comprising a microbial inhibitor, a malodor counteractant, and a fragrance. The spray or solution is applied to the bottom of footwear upon entrance to a home or other structure.

In another embodiment, the spray or solution is applied to a floor mat, such as carpeting, for example a "Welcome" mat at the front door of a home. A person upon entering the dwelling wipes his or her feet on the mat, whereupon the solution is transferred to the soles of the shoes. Please note that the spray or solution can also be applied to bare feet of either humans or animals and, when sprayed on a mat, will have the same effect on bare feet of either humans or animals.

DETAILED DESCRIPTION OF THE EMBODIMENTS

While the invention may be susceptible to embodiment in different forms, there will be described in detail, specific embodiments with the understanding that the present disclosure is to be considered an exemplification of the principles of the invention, and is not intended to limit the invention to that as illustrated and described herein.

The preferred embodiment of the present invention is a solution suitable for use in a spray bottle that will dispense the solution by squirt, spray, or mist. The solution can be dispensed by means of a positive displacement pump that moves the solution through a nozzle. The solution can alternatively be kept in a container under pressure of an inert or at least non-reactive gas and dispensed through a nozzle. In yet another embodiment, the solution can be stored in any suitable container and applied to a user's footwear, feet, floor mats, or floors by a sponge, cloth, or other applicator.

The solution of a preferred embodiment of the present invention comprises a biocide to act as a microbial inhibitor, an odor neutralizer to act as a malodor counteractant, and a fragrance, all dissolved in water.

In another embodiment, the solution comprises:
an odor neutralizer;
a chelating agent;
a preservative;
a surfactant;
a fragrance;
a tackifier;
a biocide; and
a solvent.

In another embodiment, the solution of the present invention comprises:

A odor-neutralizer comprising 0.5 to six percent by weight of the solution, preferably about 2 percent.

A chelating agent, comprising 1 to five percent by weight of the solution, preferably about 2 percent.

A preservative comprising about 0.20 percent by weight of the solution.

A surfactant comprising about 1 to 3 percent by weight of the solution, preferably about 2 percent.

A fragrance comprising about 0.1 to 0.8 by weight of the solution, preferably about 0.2 to 0.5 percent, most preferably about 0.2 to 0.3 percent.

A tackifier comprising about 0.05 percent by weight of the solution.

A biocide comprising about 0.40 percent by weight of the solution.

Water as a solvent, comprising the remainder of the solution.

In yet another embodiment, the solution of the present invention comprises:

A odor-neutralizer such as zinc ricanoleate, comprising 0.5 to six percent by weight of the solution, preferably about 2 percent.

Ethylenediaminetetraacetic acid ("EDTA") as a chelating agent, comprising 1 to five percent by weight of the solution, preferably about 2 percent.

Hexamethylenetetramine chloroallyl chloride ("Qauternium 15") as a preservative. Commercially-available products include Dowicil 200® (cis isomer only), Dowicil 75® (a mix of cis and trans isomers), and Dowicil 100® (a mix of cis and trans isomers), available from the Dow Chemical Company, comprising about 0.20 percent by weight of the solution.

The surfactant can be any generic, commercially-available surfactant, comprising about 1 to 3 percent by weight of the solution, preferably about 2 percent.

A fragrance comprising about 0.1 to 0.8 by weight of the solution, preferably about 0.2 to 0.5 percent, most preferably about 0.2 to 0.3 percent. The fragrance can be a concentrated fragrance material of a natural product, such as a flower, obtained by enfleurage, alcohol extraction or steam distillation, or can be a natural isolate of animal origin or a synthetic fragrance of similar accord. The fragrance can be a balanced complex of three or four notes that lose their individual identity to create a completely new unified odor impression. Fragrances can be obtained from Belle Aire Creations, Mundelein, Ill.

A tackifier comprising a wood rosin derivative such as a methyl ester of hydrogenated rosin, comprising about 0.05 percent by weight of the solution. One commercially-available product is Hercolyn® D from Pinova, Inc., Brunswick, Ga.

A biocide comprising a quaternary compound about 0.40 percent by weight of the solution, for example, n-alkyl dimethyl benzyl ammonium chloride and n-alkyl dimethyl ethyl benzyl ammonium chloride. One commercially-available biocide is BTC® 2125M available from Stepan Company, Northfield, Ill.

Water as a solvent, comprising about the remainder of the solution.

In any of the embodiments above, a solvent other than water can be used, including, for example, alcohols (such as methanol, ethanol, etc.) or mixtures of water and one or more alcohols.

The components as described above are mixed thoroughly to form a solution, which is stored in spray bottles or in other storage containers. In use, a user upon entering a home sprays the soles of his or her footwear with the solution, or applies the solution using an applicator such as a sponge or cloth. The solution can be applied to bare feet or to a pet's feet in the same manner.

Alternatively, the solution can be sprayed or otherwise applied directly on a mat, such as a "welcome" mat or other floor mat near an entrance. The person (or pet) entering the residence will be requested to wipe the soles of his or her footwear (or bare feet) on the mat, causing the solution to transfer to the soles of the footwear. The solution need not be used solely on a floor mat. The solution can be applied to a much larger area if desired, such as an entire entrance hall or even an entire residence.

While preferred embodiments of the present invention are shown and described, it is envisioned that those skilled in the art may devise various modifications of the present invention without departing from the spirit and scope of the appended claims.

I claim:

1. A solution for disinfecting the outer soles of footwear consisting essentially of:
   a) zinc ricinoleate as an odor neutralizer;
   b) ethylenediaminetetraacetic acid as a chelating agent;
   c) hexamethylenetetramine chloroallyl chloride as a preservative;
   d) surfactant;
   e) fragrance;
   f) a methyl ester of hydrogenated rosin as a tackifier;
   g) a quaternary ammonium biocide; and
   h) a solvent comprising water.

2. The solution of claim 1, wherein
   the zinc ricinoleate comprises 0.5 to six percent by weight of the solution;
   the ethylenediaminetetraacetic acid comprises one to five percent by weight of the solution;
   the hexamethylenetetramine chloroallyl chloride comprises about 0.20 percent by weight of the solution;
   the surfactant comprises 1 to 3 percent by weight of the solution;
   the fragrance comprises about 0.1 to 0.8 by weight of the solution
   the wood rosin derivative comprises about 0.50 percent by weight of the solution; and
   the ammonium compound comprises about 0.40 percent by weight of the solution.

3. The solution of claim 2, wherein
   the zinc ricinoleate comprises about 2 percent by weight of the solution;
   the ethylenediaminetetraacetic acid comprises about 2 percent by weight of the solution;
   the surtactant comprises about 2 percent by weight of the solution; and
   the fragrance comprises about 0.2 to 0.5 percent by weight of the solution.

4. The solution of claim 3, wherein the fragrance comprises about 0.2 to 0.3 percent by weight of the solution.

5. A container comprising a pump and nozzle and containing the solution of claim 1.

6. A container comprising a pump and nozzle and containing the solution of claim 2.

7. A container comprising a pump and nozzle and containing the solution of claim 3.

8. A container comprising a pump and nozzle and containing the solution of claim 4.

* * * * *